(12) United States Patent
Gay et al.

(10) Patent No.: US 8,247,389 B2
(45) Date of Patent: Aug. 21, 2012

(54) TREATMENT OF SCLERODERMA

(75) Inventors: Steffen Gay, Zürich (CH); Oliver Distler, Zürich (CH); Britta Maurer, Zürich (CH)

(73) Assignee: Universitat Zurich Prorektorat MNW, Zurich (CH)

( * ) Notice: Subject to any disclaimer, the term of this patent is extended or adjusted under 35 U.S.C. 154(b) by 0 days.

(21) Appl. No.: 13/061,575

(22) PCT Filed: Sep. 4, 2009

(86) PCT No.: PCT/EP2009/061454
§ 371 (c)(1),
(2), (4) Date: May 24, 2011

(87) PCT Pub. No.: WO2010/026213
PCT Pub. Date: Mar. 11, 2010

(65) Prior Publication Data
US 2011/0218233 A1    Sep. 8, 2011

(30) Foreign Application Priority Data

Sep. 4, 2008    (EP) .................................... 08015597

(51) Int. Cl.
*A61K 31/70*    (2006.01)
*C07H 21/02*    (2006.01)
*C07H 21/04*    (2006.01)

(52) U.S. Cl. ..................... 514/44 A; 536/24.1; 536/24.5
(58) Field of Classification Search .................... 514/44; 536/24.5
See application file for complete search history.

(56) References Cited

U.S. PATENT DOCUMENTS

2009/0180957 A1    7/2009    Olson et al.
2010/0285073 A1    11/2010    Olson et al.

FOREIGN PATENT DOCUMENTS

WO    2008016924 A2    2/2008
WO    2009018493 A1    2/2009

OTHER PUBLICATIONS

Maurer et al. (Arthritis and Rheumatism, 2010 vol. 62, No. 6:1733-1743).*

(Continued)

*Primary Examiner* — Terra Cotta Gibbs
(74) *Attorney, Agent, or Firm* — Millen, White, Zelano, Branigan, P.C.

(57) ABSTRACT

The present invention provides a method of treating scleroderma. The method consists in the upregulation of miR-29 by administration of miR-29 or a miR-29 upregulator which elevates circulating and/or intracellular concentrations of miR-29. The invention likewise relates to the use of miR-29 for such a treatment, and the use of miR-29 for the manufacture of a medicament for the treatment of scleroderma.

7 Claims, 4 Drawing Sheets

OTHER PUBLICATIONS

Letter to the Editor/Journal of Dermatological Science, 2011 vol. 61:67-69.*

Maurer et al. MicroRNA 29a6—a Critical Regulator of Fibrotic Mechanisms in SSc. Presentation at the American College of Rheumatology (2008). Abstract. Sep. 8, 2008.*

Maurer et al. (Arthritis & Rheumatism, 2010 vol. 62, No. 6:1733-1743).*

Chabaud et al. (International Journal of Rheumatology, 2011, Article ID 495792, 13 pages).*

Van Rooij Eva et al. "Dysregulation of microRNAs after myocardial infarction reveals a role of miR-29 in cardiac fibrosis." (Proceedings of the National Academy of Sciences of the United States of America) pp. 13027-13032, vol. 105, No. 35, Sep. 2, 2008.

Sengupta Srikumar et al. "MicroRNA 29c is down-regulated in nasopharyngeal carcinomas, up-regulating mRNAs encoding extracellular matrix proteins." (Proceedings of the National Academy of Sciences of the United States of America) pp. 5874-5878, vol. 105, No. 15, Apr. 15, 2008.

Varga J et al. "Modulation of collagen gene expression: its relation to fibrosis in systemic sclerosis and other disorders." (Annals of Internal Medicine) pp. 60-62, vol. 122, No. 1, Jan. 1, 1995.

Varga J et al. "Regulation of connective tissue synthesis in systemic sclerosis." (International Reviews of Immunology) pp. 187-199, vol. 12, No. 2-4, 1995.

Maurer Britta et al. "MicroRNA 29a—a critical regulator of fibrotic mechanisms in SSc" (Arthritis and Rheumatism) p. S596, vol. 58, No. 9, Sep. 8, 2008.

World IP Organization. "International Search Report." PCT/EP2009/061454, Applicant: Universitat Zuerich Prorektorat MNW, Mailed: Apr. 9, 2010.

* cited by examiner

A

B

A

B

SEQUENCE LISTING

```
<160> NUMBER OF SEQ ID NOS: 18

<210> SEQ ID NO 1
<211> LENGTH: 22
<212> TYPE: RNA
<213> ORGANISM: Homo sapiens

<400> SEQUENCE: 1
uagcaccauc ugaaaucggu ua                                           22

<210> SEQ ID NO 2
<211> LENGTH: 23
<212> TYPE: RNA
<213> ORGANISM: Homo sapiens

<400> SEQUENCE: 2
uagcaccauu ugaaaucagu guu                                          23

<210> SEQ ID NO 3
<211> LENGTH: 23
<212> TYPE: RNA
<213> ORGANISM: Homo sapiens
```

-continued

<400> SEQUENCE: 3
uagcaccauu ugaaaucagu guu          23

<210> SEQ ID NO 4
<211> LENGTH: 22
<212> TYPE: RNA
<213> ORGANISM: Homo sapiens

<400> SEQUENCE: 4
uagcaccauu ugaaaucggu ua           22

<210> SEQ ID NO 5
<211> LENGTH: 21
<212> TYPE: RNA
<213> ORGANISM: Homo sapiens

<400> SEQUENCE: 5
uagcaccauc ugaaaucggu u            21

<210> SEQ ID NO 6
<211> LENGTH: 23
<212> TYPE: RNA
<213> ORGANISM: Homo sapiens

<400> SEQUENCE: 6
uagcaccauu ugaaaucagu guu          23

<210> SEQ ID NO 7
<211> LENGTH: 20
<212> TYPE: RNA
<213> ORGANISM: Homo sapiens

<400> SEQUENCE: 7
uagcaccauu ugaaaucggu              20

<210> SEQ ID NO 8
<211> LENGTH: 42
<212> TYPE: RNA
<213> ORGANISM: Homo sapiens

<400> SEQUENCE: 8
cgcaaggaug acacgcaaau ucgugaagcg uuccauauuu uu          42

<210> SEQ ID NO 9
<211> LENGTH: 22
<212> TYPE: RNA
<213> ORGANISM: Homo sapiens

<400> SEQUENCE: 9
uagcaccauc ugaaaucggu ua           22

<210> SEQ ID NO 10
<211> LENGTH: 23
<212> TYPE: RNA
<213> ORGANISM: Homo sapiens

<400> SEQUENCE: 10
uagcaccauu ugaaaucagu guu          23

<210> SEQ ID NO 11
<211> LENGTH: 22
<212> TYPE: RNA
<213> ORGANISM: Homo sapiens -continued

<400> SEQUENCE: 11
uagcaccauu ugaaaucggu ua                                        22

<210> SEQ ID NO 12
<211> LENGTH: 21
<212> TYPE: DNA
<213> ORGANISM: Artificial
<220> FEATURE:
<223> OTHER INFORMATION: Collagen expression primer

<400> SEQUENCE: 12
tcaagagaag gctcacgatg g                                         21

<210> SEQ ID NO 13
<211> LENGTH: 20
<212> TYPE: DNA
<213> ORGANISM: Artificial
<220> FEATURE:
<223> OTHER INFORMATION: Collagen expression primer

<400> SEQUENCE: 13
tcacggtcac gaaccacatt                                           20

<210> SEQ ID NO 14
<211> LENGTH: 19
<212> TYPE: DNA
<213> ORGANISM: Artificial
<220> FEATURE:
<223> OTHER INFORMATION: Collagen expression primer

<400> SEQUENCE: 14
ggcatgccac agggattct                                            19

<210> SEQ ID NO 15
<211> LENGTH: 21
<212> TYPE: DNA
<213> ORGANISM: Artificial
<220> FEATURE:
<223> OTHER INFORMATION: Collagen expression primer

<400> SEQUENCE: 15
gcagccccat aatttggttt t                                         21

<210> SEQ ID NO 16
<211> LENGTH: 20
<212> TYPE: DNA
<213> ORGANISM: Artificial
<220> FEATURE:
<223> OTHER INFORMATION: Primer for cloning of seed match fragments

<400> SEQUENCE: 16
acgcaaggct gtgagactac                                           20

<210> SEQ ID NO 17
<211> LENGTH: 23
<212> TYPE: DNA
<213> ORGANISM: Artificial
<220> FEATURE:
<223> OTHER INFORMATION: Primer for cloning of seed match fragments

<400> SEQUENCE: 17
cattgagcat tatctctact ctg                                       23

<210> SEQ ID NO 18
<211> LENGTH: 33
<212> TYPE: DNA

-continued

```
<213> ORGANISM: Artificial
<220> FEATURE:
<223> OTHER INFORMATION: Primer for cloning of seed match fragments

<400> SEQUENCE: 18
gtaattctag aaccaaactc tatctgaaat ccc                                    33
```

TREATMENT OF SCLERODERMA

FIELD OF THE INVENTION

The present invention relates to a novel pharmacological treatment of scleroderma. Specifically the invention relates to the upregulation of the microRNA family miR-29 to treat scleroderma.

BACKGROUND OF THE INVENTION

The present invention relates to a novel pharmacological treatment of scleroderma SSc. There are different types of scleroderma. The multi-systemic fibrotic form, also called systemic sclerosis, comprises two sub-types depending on the degree of skin involvement: The limited cutaneous form affects the extremities whereas the diffuse subtype also involves the trunk. Besides the systemic disease, there are localized forms of the disease including e.g. morphea, that involve certain areas of the skin, sometimes joints and muscles, but not the internal organs. The major hallmarks of systemic sclerosis are widespread microvascular damage and progressive fibrosis of the skin and internal organs. The most evident clinical symptom is usually the hardening of the skin and associated scarring. The skin may appear tight, reddish or scaly. Despite the progress in managing complications which occur mostly due to organ failure, to date, there is still neither cure nor disease-specific treatment. Even though some currently available drugs may soften the skin and reduce inflammation, there is clearly a need for additional and efficacious medicaments for the treatment of scleroderma.

miR-29 is a small non-coding micro RNA that is involved in regulating gene expression. Animal miRNAs are transcribed as an approximately 70 nucleotide precursor and subsequently processed by the Dicer enzyme to give a product with approximately 22 nucleotides. In this case the mature sequence comes from the 3' end of the precursor RNA. The products are thought to have regulatory roles through complementarity to the 5' end of the target mRNA. To the miR-29 family belong miR-29a, miR-29b1 and miR29b2, and miR-29c.

It has been shown that miR-29 regulates the level of the Mcl-1 protein, an anti-apoptotic member of the Bcl-2 family of proteins. Furthermore it has been shown that miR-29 regulates the level of Tcl1 protein, an oncogene found to be disrupted in many T-cell leukemias, and directly targets both DNMT3A and DNMT-3B which are frequently upregulated in lung cancer. Furthermore it has been shown that in the absence of miR-208, miR-29 expression is upregulated, preventing cardiac fibrosis (WO 2008/074866). The role of miR-29 in skin cells and in scleroderma has so far not been investigated.

SUMMARY OF THE INVENTION

The present invention provides a method of treating fibrosis in scleroderma, comprising administration to a patient in need thereof a therapeutically effective amount of miR-29 or a miR-29 upregulator. Furthermore the invention relates to the use of miR-29 or miR-29 upregulators for such a treatment, and to the use of miR-29 or miR-29 upregulators for the manufacture of a medicament for the treatment of scleroderma and to a method of screening for a compound effective in the treatment of scleroderma.

DETAILED DESCRIPTION OF THE INVENTION

Figure 1:
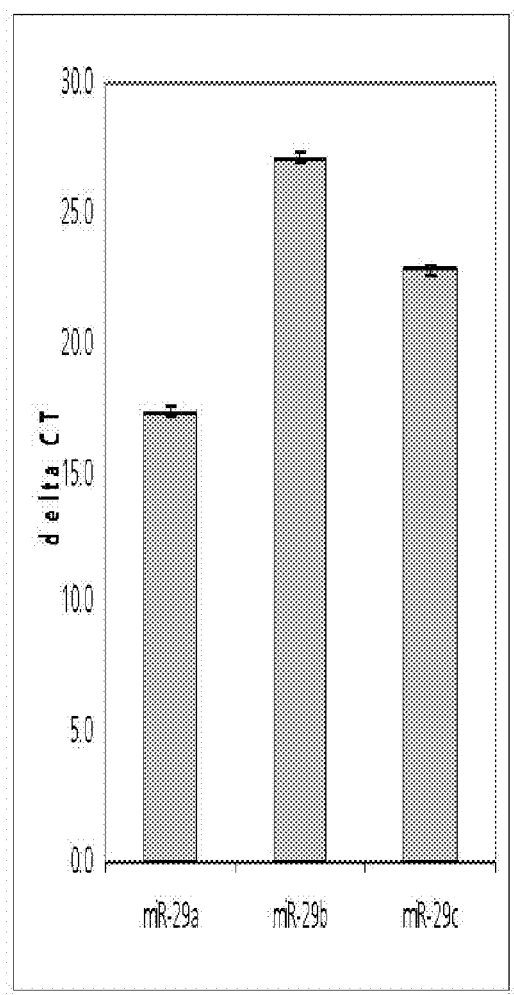
FIG. 1:
A: Baseline expression of the miR-29 family in SSc fibroblasts: The expression is strongest for miR-29a (in the delta ct-method low numbers mean high expression).
B: The baseline expression levels of the miR-29 family members are strongly downregulated in SSc skin fibroblasts compared to normal skin fibroblasts (n=6 each).
Figure 1:
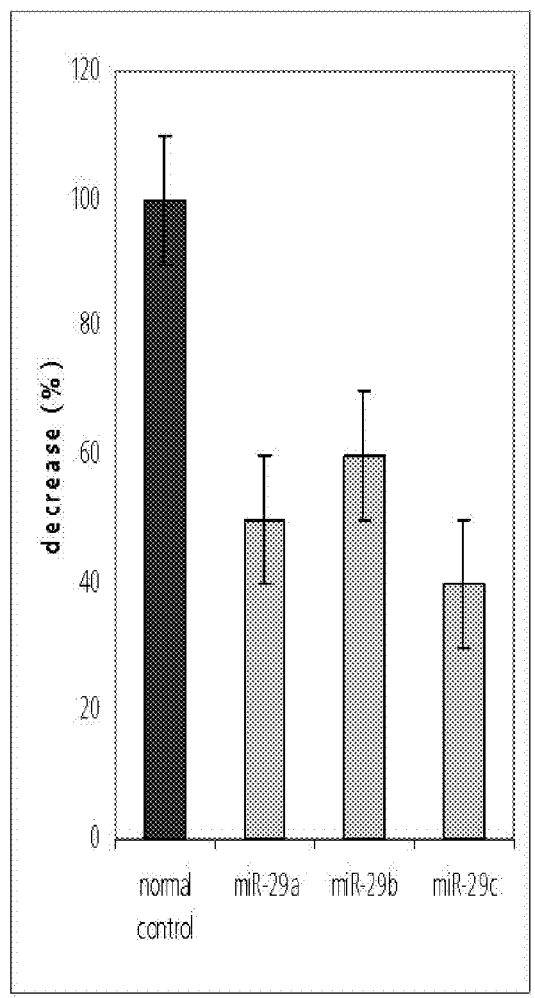

The present invention provides a method of treating scleroderma. Scleroderma includes a multi-systemic form and localized forms that include but are not limited to morphea. The inventive treatment comprises administering to a patient in need thereof a therapeutically effective amount of miR-29 or a miR-29 upregulator. It involves an elevation of circulating and/or intracellular concentrations of miR-29.

miR-29 includes mature miR-29 a, miR-29 b1, miR-29b2 and miR-29c as well as homologous sequences, precursors, fragments or variants thereof that retain the biological activity of the mature miRNA's. Also included are other nucleic acids such as DNA encoding the aforesaid sequences. Homology is generally inferred from sequence similarity between two or more nucleic acids. The precise percentage of similarity between sequences that is useful to establishing homology varies with the nucleic acid at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g. BLASTN using default parameters) are generally available.

The RNA sequences of the miR-29 family are as follows:
Mature miR-29a: UAGCACCAUCUGAAAUCGGUUA
Mature miR-29b1: UAGCACCAUUUGAAAUCAGUGUU
Mature miR-29b2: UAGCACCAUUUGAAAUCAGUGUU
Mature miR-29c: UAGCACCAUUUGAAAUCGGUUA
A preferred miR-29 according to the invention is miR-29a as well as homologous sequences, precursors, fragments or variants thereof that retain the biological activity of the mature miR-29a.

miR-29 upregulators are compounds which increase the expression and/or activity of miR-29 in blood or cells and include, but are not limited to, vectors that express miR-29.

Examples of expression vectors are viral expression vectors such as an adenoviral or retroviral expression vector.

The administration of miR-29 or a miR-29 upregulator may be by any method known to those in the art suitable for delivery to skin and internal organs. For example, in certain aspects of the invention, miR-29 or the miR-29 upregulator may be administered by intravenous injection or intraarterial injection. In some aspects, administering comprises oral, transdermal, intraperitoneal, subcutaneous, sustained release, controlled release, delayed release, suppository, or sublingual administration of miR-29 or the miR-29 upregulator.

The dosage of the active ingredient depends upon the species, its age, weight, and individual condition, the individual pharmacokinetic data, and the mode of administration. In the case of an individual having a bodyweight of about 70 kg the daily dose administered of miR-29 or an miR-29 upregulator is from 0.01 mg/kg bodyweight to 1000 mg/kg bodyweight, preferred is 0.1 mg/kg bodyweight to 100 mg/kg bodyweight, more preferred from 1 mg/kg to 25 mg/kg bodyweight, administered as a single dose or as several doses. miR-29 or an miR-29 upregulator can be used alone or in combinations with other drugs.

Furthermore the invention relates to the use of miR-29 or an miR-29 upregulator, in particular the use of a pharmaceutical composition comprising an miR-29 or an miR-29 upregulator, for the treatment of scleroderma.

The invention likewise relates to the use of miR-29 or an miR-29 upregulator for the manufacture of a medicament for the treatment of scleroderma.

The medicaments of the present invention are pharmaceutical compositions prepared in a manner known per se, for example by means of conventional mixing, granulating, coating, dissolving or lyophilizing processes. In certain aspects of the invention, miR-29 or the miR-29 upregulator are associated with a lipid vehicle. Alternatively, one may simply provide miR-29 or the miR-29 upregulator by itself, optionally included within a delivery vehicle, such as a liposome or nanoparticle. In certain aspects of the invention, miR-29 or the miR-29 upregulator are prepared in an ointment.

The invention further relates to a method of screening for a compound effective in the treatment of scleroderma comprising i) contacting a candidate compound with a fibroblast, and ii) assessing miR-29 activity or expression, and iii) choosing candidate compounds which selectively increase activity or expression of miR-29 compared to activity or expression in the absence of the candidate compound. Assessing the activity or expression may comprise assessing the expression level of miR-29. Those in the art will be familiar with a variety of methods for assessing RNA expression levels, including, for example, northern blotting or RT-PCR. The invention further relates to compounds selected by these methods of screening.

The following examples serve to illustrate the invention without limiting the invention in its scope. These data demonstrate inter alia that miR-29 is down-regulated in skin-samples of scleroderma patients compared to healthy controls and accordingly indicates that upregulation of miR-29 is useful for the treatment of scleroderma.

Example 1

Baseline Expression of the miR-29 Family in Cultured SSc Fibroblasts Compared to Normal Skin Fibroblasts Skin biopsy specimens from SSc patients and healthy donors were obtained by punch biopsy. All patients fulfilled the criteria for SSc as suggested by LeRoy at al. For all in vitro experiments that are described within this application, skin fibroblasts from outgrowth cultures were cultured in T75 flasks. The skin fibroblasts were maintained in DMEM/10% FCS, and passages 3-8 were used for analysis.

Expression levels of miR-29s were analysed in SSc patients compared to healthy controls using Taqman-based RT-PCR after isolation of RNA using the miRVana kit (Ambion/Applied Biosystems). Specific single Taqman MicroRNA Assays from Ambion/Applied Biosystems were used. The target sequences were as follows: hsa-miR-29a: UAGCACCAUCUGAAAUCGGUU (assay ID: 000412, part no.: 4373065), hsa-miR-29b: UAGCACCAUUUGAAAU-CAGUGUU (assay ID: 000413, part no.: 4373288), hsa-miR-29c: UAGCACCAUUUGAAAUCGGU (assay ID: 000415, part no.: 4373289), RNU6B (endogenous control): CGCAAGGAUGACACGCAAA-UUCGUGAAGCGUUCCAUAUUUUU (assay ID: 001093, part no.: 4373381).

As measured by the delta ct-method where low numbers mean high expression, all members of the miR-29 family were found to be expressed in SSc fibroblasts, and within the miR-29 family, miR-29a showed the highest expression (delta ct=17.4±0.2) compared to miR-29b (delta ct=27.1±0.3) or to miR-29c (ct=22.8±0.1), see FIG. 1A. Compared to healthy controls, the baseline levels of miR-29 were consistently downregulated in cultured SSc fibroblasts (mir-29a: p=0.012, miR-29b: p=0.046, miR-29c: p=0.028), see FIG. 1B.

All data within this application are provided as mean±standard error of the mean. P-values<0.05 are considered statistically significant.

Example 2

Figure 2:
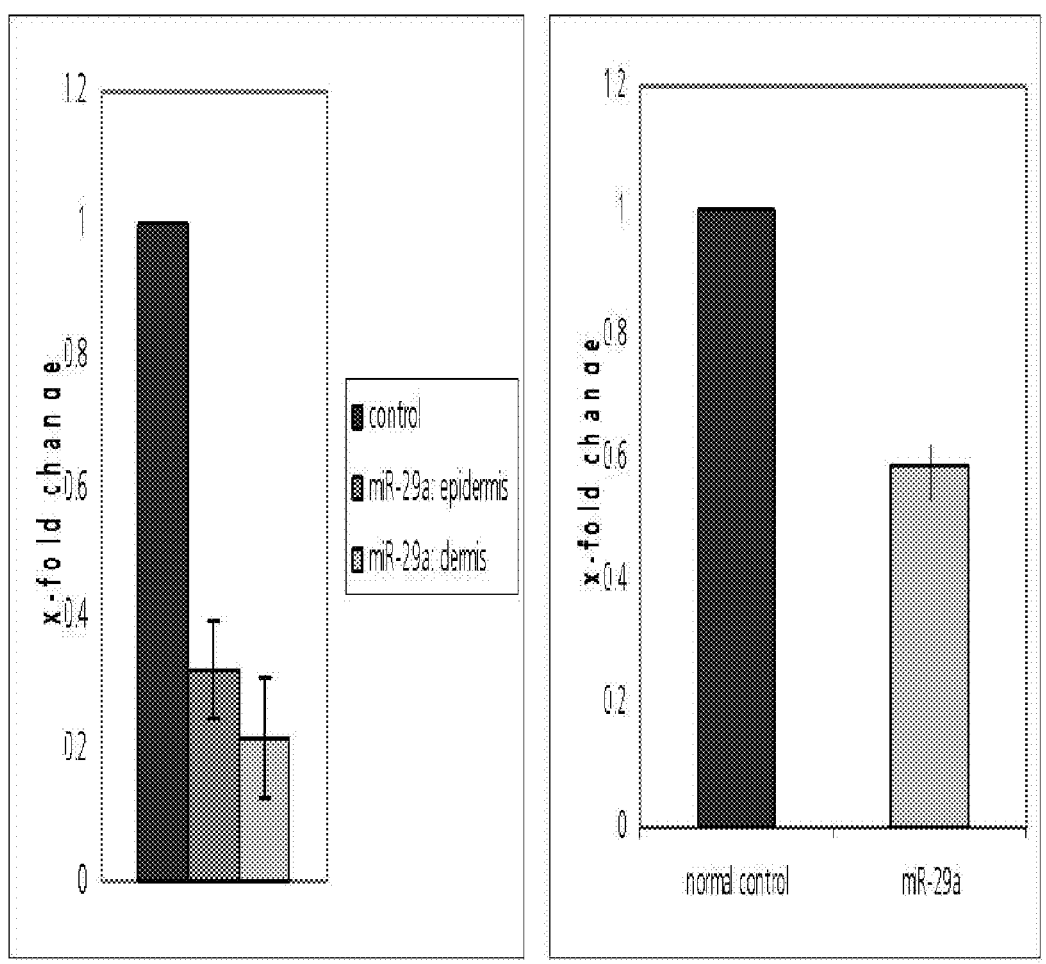
FIG. 2:
A: The baseline expression of miR-29a in paraffin embedded skin sections from SSc patients is downregulated compared to healthy controls. There is no difference in the expression between the epidermal and the dermal layer.
B: The baseline expression of miR-29a in fresh skin biopsies of SSc patients is downregulated compared to healthy controls.

Baseline Expression of miR-29a in a) Paraffin Sections and b) Skin Biopsies of SSc Patients Compared to Healthy Controls The baseline expression of miR-29a was investigated in ex vivo samples of SSc patients compared to healthy controls. After homogenization with a tissue lyser, RNA was isolated using the miRVana kit (Ambion/Applied Biosystems) and employed Taqman-based RT-PCR. The aforementioned specific single Taqman MicroRNA Assays for miR-29a and RNU6B from Ambion/Applied Biosystems were used.

a) To assess potential differences in the expression levels between the epidermal and the dermal layer, first RNA was analyzed which was isolated from paraffin embedded tissue sections using the RecoverAll Total Nucleic Acid isolation kit (Ambion/Applied Biosystems) after epidermis and dermis had been dissected. In the tissue again a very strong expression of miR-29a (delta ct=18) was found, and compared to normal controls it was significantly downregulated both in epidermis and dermis of SSc patients (p=0.012), see FIG. 2A.

b) To exclude potentially misleading influences due to the paraffin treatment of the samples, additionally the expression of miR-29a in fresh skin biopsies from SSc patients was investigated and healthy controls that had been stored in RNA later at −20° C. shorter than 2 years. Again, miR-29a was significantly downregulated in SSc compared to healthy controls (p=0.042), see FIG. 2B.

Example 3

Enforced Expression of miR-29 in SSc Fibroblasts Downregulates the Expression of Collagen 1 and 3 on mRNA and Protein Level To assess the effects of miR-29 on collagen expression in skin fibroblasts and above all to prove that the miR-29 family members could alter the collagen expression in SSc, SSc skin fibroblasts were transfected in 6-well plates with 100 nM (final concentration) of pre-miR-29a, pre-miR-29b, and pre-miR-29c or scrambled controls using Lipofectamine 2000 reagent (Invitrogen) to examine whether the overexpression of miR-29a led to the downregulation of collagen genes. The following precursor molecules and negative controls from Ambion/Applied Biosystems were employed: pre-miR-29a (product ID: PM12499, mature miRNA sequence: UAGCACCAUCUGAAAUCGGUUA), pre-miR-29b-2 (product ID: PM10103, mature miRNA sequence: UAGCACCAUUUGAAAUCAGUGUU), pre-miR-29c (product ID: PM10518, mature miRNA sequence: UAGCACCAUUUGAAAUCGGUUA), pre-miR miRNA precursor molecules-negative control #1 (part no.: 17110). The expression of collagen 1 and 3 was analyzed on mRNA level by Taqman-based RT-PCR using Sybr Green Primers. The primer sequences were as follows: Procollagen 1A1 fwd: 5'-TCAAGAGAAGGCTCACGATGG-3', rev.: 5'-TCACGGTCACGAACCACATT-3'; Procollagen 3A1 fwd: 5'-GGCATGCCACAGGGATTCT-3', rev.: 5'-GCAGCCCCATAATTTGGTTTT-3'. The effects of the overexpression of miR-29a on collagen 1A1 and 3A1 on protein level were examined by Western Blot according to standard protocols. The primary antibodies were purchased from Santa Cruz Biotechnologies (collagen 1 (H-70): sc-28655, lot # B2406; collagen 3 (H-300): sc-28888, lot # K2205).

Figure 3:
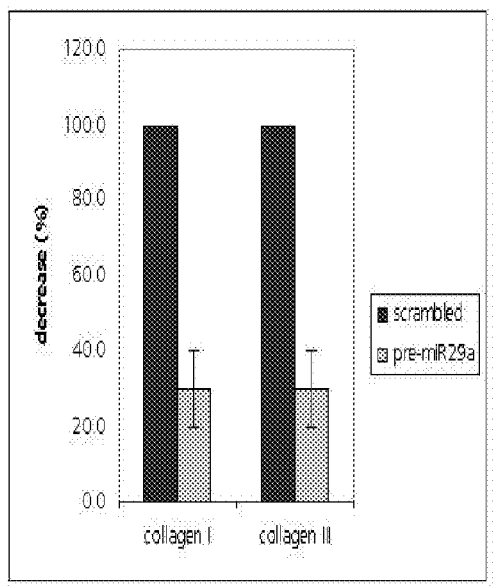
FIG. 3:
A: The enforced expression of miR-29a in SSc skin fibroblasts results in downregulation of collagen 1 and 3 on mRNA and on protein level 72 h after transfection.
B: The enforced expression of miR-29b and miR-29c in SSc skin fibroblasts results in downregulation of collagen 1 and 3 on mRNA level 72 h after transfection.
Figure 3:
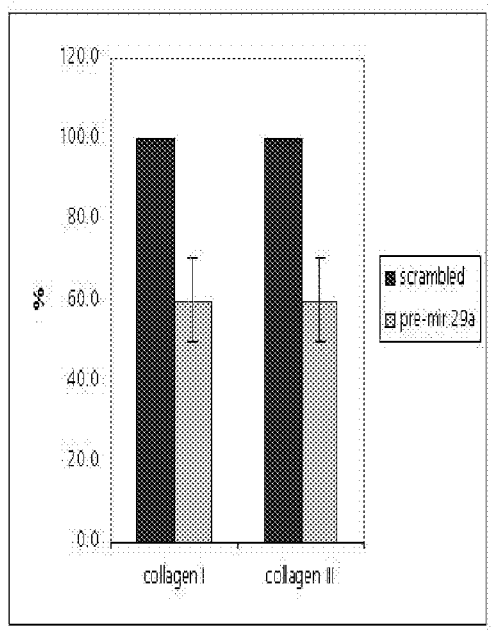
Figure 3:
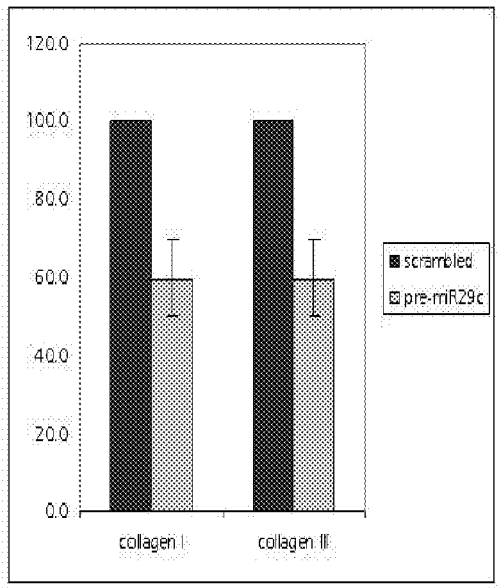
Figure 3:
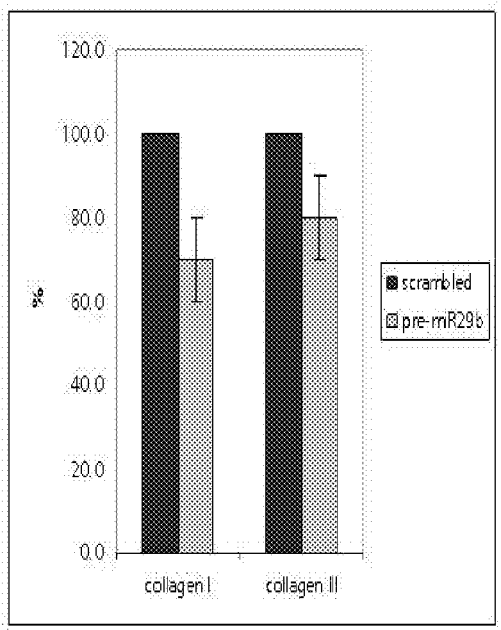

The enforced expression of miR-29a in SSc skin fibroblasts induced a remarkable downregulation of collagen 1 and 3 expression on mRNA level (p=0.043 each) as well as on protein level (p=0.027) as analyzed by semiquantitative densitometry. Overexpression of miR-29b and miR-29c in SSc fibroblasts resulted also in downregulation of collagen I and III on mRNA level, see FIG. 3.

In summary, these functional experiments provide robust evidence that the miR-29 family negatively regulates major pathogenic pathways in SSc.

Example 4

Luciferase Reporter Assay for Targeting the 3' UTR of Col3A1

To demonstrate that the miR-29 family members, and in particular miR-29a, are direct regulators of collagen gene expression in skin fibroblasts and to prove that the effects on gene regulation were not mediated by targeting further mediators, we performed a luciferase reporter assay for targeting the 3'UTR of Col3A1 that harbours 2 bindings sites for each of the miR-29 family members: a conserved binding site at position 242-249 of COL3A1 3'UTR and a poorly conserved binding site at position 682-689 (information provided by TargetScan database, release 4.2; http://www.targetscan.org/). For the experiment, a Col3A1 3'UTR segment of 973 basepairs was amplified by PCR from human genomic DNA and inserted into the pGL3-control vector with simian virus 40 promoter (Promega) by using the XbaI site immediately downstream from the stop codon of luciferase. We designed specific primers to generate specific fragments harbouring the predicted match seed of miR-29s. The primer sequences were as follows: Col3A1-3'UTR fwd: 5'-ACGCAAGGCTGTGAGACTAC-3', Col3A1-3'UTR rev.: 5'-CATTGAGCATTATCTCTACTCTG-3', Col3A1 XbaI fwd: 5'-GTAATTCTAGAACCAAACTCTATCTGAAATCCC-3'. SSc or normal skin fibroblasts were co-transfected in 6-well plates by using Lipofectamine 2000 reagent (Invitrogen) according to the instructions of the manufacturer, with 0.375 ug of the firefly luciferase report vector and 0.2 ug of the control vector containing Renilla luciferase pRL-SV40 vector (Promega). For each well, 100 nM pre-miR29a, 29b, 29c or scrambled control (Ambion/Applied Biosystems) was used. Firefly and Renilla luciferase activities were measured by using dual-luciferase assays (Promega) 24 h after the transfection. The experiments were performed in duplicate.

Figure 4:
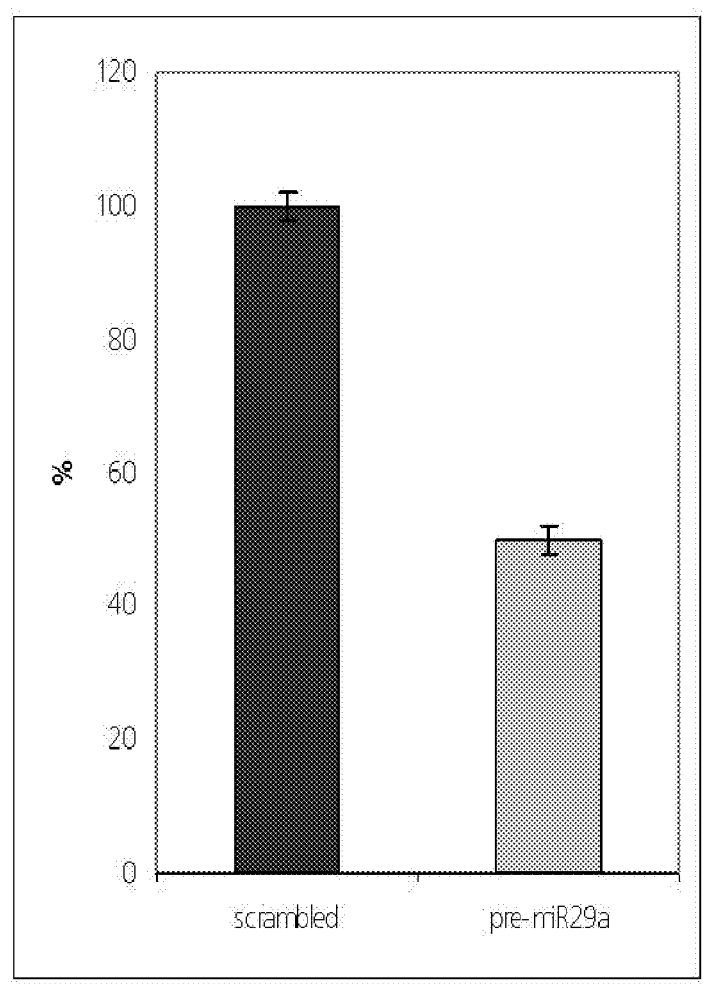
FIG. 4:
Luficerase reporter gene assay targeting Col3A1-3'UTR: Co-transfection with pGL3 control/3'UTR_Col3A1__5' to 3' and pre-miR29a results in a decrease of the firefly luciferase activity.

The results show that the co-transfection with pre-miR29a decreased the firefly luciferase activity by approx. 50% thus providing evidence of a direct regulatory effect without any other mediating molecules, see FIG. 4.

The invention claimed is:

1. A method of treating scleroderma, comprising administering to a patient in need thereof a therapeutically effective amount of miR-29 or a miR-29 upregulator.

2. The method according to claim 1, wherein the miR-29 upregulator is an expression vector expressing miR-29.

3. The method according to claim 1, wherein the miR-29 is miR-29 a, miR-29 b1, miR-29b2, miR-29c or a combination thereof.

4. The method according to claim 3, wherein the combination comprises miR-29b and miR-29c.

5. The method according to claim 1, wherein the miR-29 is
 (a) mature miR-29a which comprises the RNA sequence set forth in SEQ ID NO: 1 or a DNA equivalent thereof,
 (b) mature miR-29b1 which comprises the sequence set forth in SEQ ID NO: 2 or a DNA equivalent thereof,
 (c) mature miR-29b2 which comprises the sequence set forth in SEQ ID NO: 3 or a DNA equivalent thereof, or
 (d) mature miR-29c which comprises the sequence set forth in SEQ ID NO: 4 or a DNA equivalent thereof.

6. The method according to claim 1, wherein the miR-29 is
 (a) pre-miR-29a,
 (b) pre-miR-29b-2, or
 (c) pre-miR-29c.

7. The method according to claim 1, wherein the patient is a human patient.

* * * * *